United States Patent [19]

Gass

[11] 4,220,770
[45] Sep. 2, 1980

[54] TRIAZINE COMPOUNDS

[75] Inventor: Karl Gass, Magden, Switzerland

[73] Assignee: Ciba-Geigy Corporation, Ardsley, N.Y.

[21] Appl. No.: 894,448

[22] Filed: Apr. 7, 1978

[30] Foreign Application Priority Data

Apr. 14, 1977 [CH] Switzerland .................. 4629/77

[51] Int. Cl.² .............. C07D 251/50; C07D 251/52; C07D 251/54
[52] U.S. Cl. ............................ 544/208; 544/197; 71/93
[58] Field of Search ............... 544/208, 197; 71/93

[56] References Cited

U.S. PATENT DOCUMENTS

| | | | |
|---|---|---|---|
| 3,583,987 | 6/1971 | Berrer et al. | 260/249.6 |
| 3,629,256 | 12/1971 | Berrer et al. | 260/249.8 |
| 3,629,257 | 12/1971 | Berrer et al. | 260/249.8 |
| 3,629,258 | 12/1971 | Berrer et al. | 260/249.8 |
| 3,830,810 | 8/1974 | Berrer et al. | 544/208 |

FOREIGN PATENT DOCUMENTS 1327060 8/1973 United Kingdom .

*Primary Examiner*—John M. Ford
*Attorney, Agent, or Firm*—Harry Falber

[57] ABSTRACT

The present invention discloses new herbicidally active triazine compounds of the formula

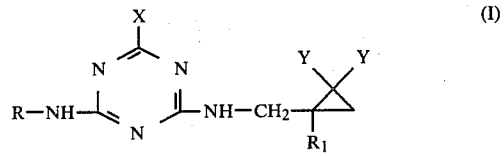
(I)

wherein R represents hydrogen, $C_1$-$C_6$ alkyl which is unsubstituted or substituted by cyano, hydroxy, $C_1$-$C_4$ alkoxy, cyclopropyl, methylcyclopropyl, or a radical

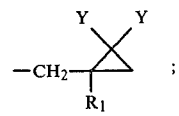

wherein
$R_1$ represents hydrogen or methyl
X represents chlorine, methoxy, methylthio, azido or cyano and
Y represents a halogen atom.

These compounds are particularly useful for controlling weeds in crops of rice.

4 Claims, No Drawings

TRIAZINE COMPOUNDS

The present invention relates to novel herbicidally active triazine compounds, processes for the production thereof, and herbicidal compositions which contain these compounds as active component, as well as a method of controlling undesired plant growth, especially for selectively controlling weeds in crops of rice, which comprises the use of the novel triazine compounds or of compositions containing them.

The novel triazine compounds have the general formula I

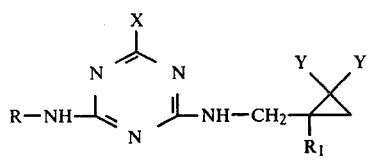

wherein
R represents hydrogen, $C_1$-$C_6$alkyl which is unsubstituted or substituted by cyano, hydroxyl, $C_1$-$C_4$alkoxy, cyclopropyl, methylcyclopropyl, cyclopropylmethyl, or a radical

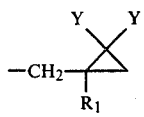

wherein
$R_1$ represents hydrogen or methyl,
X represents chlorine, methoxy, methylthio, azido or cyano and
Y represents a halogen atom.

In the compounds of the formula I, alkyl radicals R are to be understood as meaning straight-chain and branched radicals of 1 to 6 carbon atoms, such as the methyl, ethyl, n-propyl or isopropyl, n-butyl, sec-butyl, isobutyl or tert-butyl radical, a branched or the unbranched pentyl or hexyl radical. These radicals can be substituted by the cyano group or a $C_1$-$C_4$alkoxy group. The methylcyclopropyl group can be both the 1-methylcyclopropyl and the 2-methylcyclopropyl group and also the cyclopropylmethyl radical. The preferred halogen atom Y is chlorine.

The novel s-triazines of the formula I have excellent herbicidal properties and are suitable in particular for the selective control of grass-like and dicotyledonous weeds in a very wide variety of cultivated plants. When used in high concentration, the novel compounds have a total herbicidal action, and in low concentrations they have a selective action. They can therefore be used as selective herbicides for the control of weeds in crops of different cultivated plants, such as cereals, for example wheat, barley, rye, oats, sorghum, as well as in maize, rice and sugar cane, cotton, soya, sugar beet and leguminosae. The action of the novel compounds against weeds in rice crops is of particular interest.

The s-triazines of the present invention can be used both in the preemergent and the post-emergent method for controlling grass-like and dicotyledonous weeds. Tests have shown that the novel compounds can be used for example to destroy obstinate weeds in arable pastures, and their representatives, such as panic-grass species (Panicum sp.), mustard species (Sinapis sp.), goosefoot species (Chenopodiaceae), and also grasses (Gramineae), umbelliferae and mayweed species (Matricariae), without harming useful plants, such as cereals, rice, maize and sorghum, in their germination and growth.

These triazine compounds are also able to inhibit the growth of dicotyledonous and grass-like plants. They can therefore also be used wherever mowing is to be economised on, for example in areas of grass on sports fields or on the verges of main roads and railway lines, and in addition in shrubs and hedgerows.

A further use of the novel triazine compounds is the burning over of leaves and parts of plants above the soil shortly before harvesting in crops such as cotton or potatoes, in order to facilitate harvesting.

The compounds of the present invention are new. These compounds, or the halogenated cyclopropylamines used as intermediates, have to our knowledge not been previously manufactured. Triazine compounds which contain the cyclopropylamine in the molecule are known from Swiss Pat. Nos. 492,397 to 492,400 and 518,293 as well as from Belgian Pat. No. 714,891. These compounds appear to be active, strong herbicides which are non-harmful to maize. But none of these compounds are used to our knowledge for the selective control of weeds in rice crops.

The novel triazine compounds of the formula I are obtained according to the invention by reacting, in accordance with the following reaction scheme, cyanuric chloride in a first step at a temperature of $-20°$ to $+10°$ C., in an inert solvent or diluent, with an equimolar amount of an amine of the formula II or III, in the presence of an equimolar amount of an acid acceptor, and then in a second step, at a temperature of $0°$-$50°$ C., in an inert solvent, in the presence of an equimolar amount of an acid acceptor, with the equimolar amount of the other amine of the formula II or III. If X in the final product is not chlorine, the resulting 2-chloro-4,6-diamino-s-triazine of the formula V is reacted at elevated temperature with a salt of methanol, methylthiol, cyanic acid or with an azide, which may be first prepared in situ.

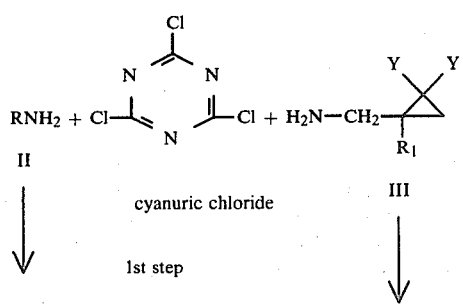

-continued

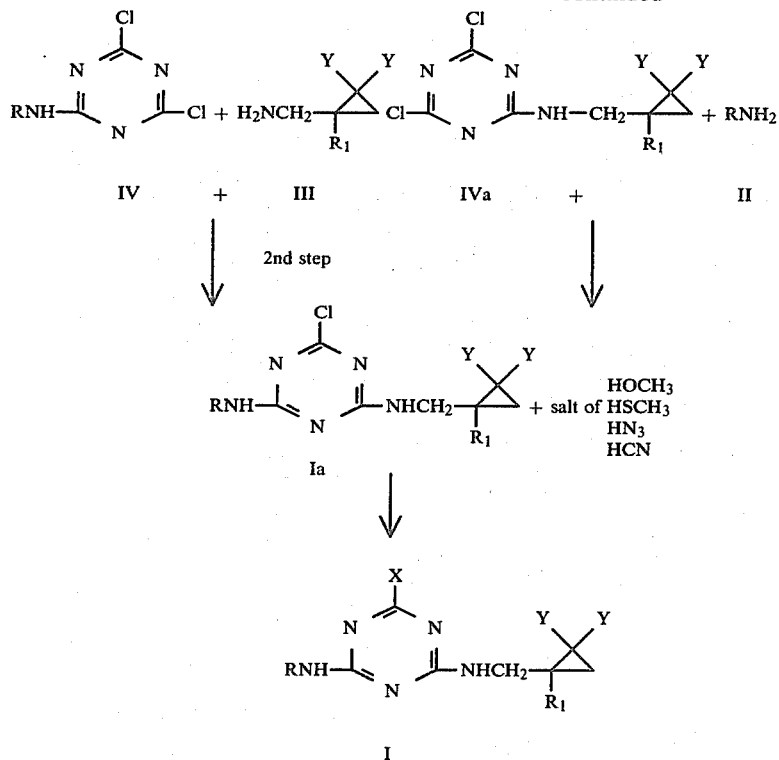

In the above formulae, R, R$_1$ and Y are as defined in formula I.

The reaction is advantageously carried out in the presence of a solvent or diluent which is inert to the reactants. Examples of such solvents and diluents are aromatic hydrocarbons and halogenated hydrocarbons as well as aliphatic hydrocarbons, ketones, acid esters, and also mixtures thereof with water.

The reactions with the amines of the formulae II and III are carried out in the presence of the equimolar amount of an acid acceptor, for example an inorganic base, such as an alkali metal hydroxide, for example sodium hydroxide, or a tertiary amine or an excess of the amine employed.

In the first step, the reaction temperatures are between $-30°$ and $+10°$ C., preferably between $-20°$ and $-10°$ C., whereas for the second step a higher temperature between $0°$ and $40°$ C., preferably between $20°$ and $30°$ C., is used.

The compounds of the formula I, in which X represents methoxy, can be prepared by reacting a 2-chloro-4,6-diamino-s-triazine of the formula Ia in an inert anhydrous solvent with an alkali metal salt of methanol, such as sodium methanolate. The reaction is preferably also carried out in absolute methanol, in the presence of metallic sodium or sodium hydride. The methoxytriazine can also be prepared by heating the chlorotriazine of the formula Ia in a methanolic solution in the presence of a condensation agent, such as triethylamine.

The substitution of the methylthio group for the chlorine atom is effected by treating a 2-chloro-4,6-diamino-s-triazine of the formula Ia in a diluent, for example acetone/water, with an aqueous solution of triethylamine and introducing gaseous methyl mercaptan, or by adding the chloro-s-triazine to an alcoholic or alcoholic-aqueous solution of an alkali metal mercaptide and heating this mixture until it shows neutral reaction.

These compounds can also be prepared by using equimolar amounts of 2-chloro-4,6-diamino-s-triazine of the formula Ia, thiourea and dimethyl sulphate.

It is possible to introduce the azido group by reacting 2-chloro-4,6-diamino-triazine of the formula Ia with an alkali metal azide, optionally in the presence of triethylamine, and, by reacting it with an alkali metal cyanide or another metal salt of cyanic acid, to introduce the cyano group. Preferably a mixture of acetone/water is used as solvent or diluent for the reaction. However, it is also possible to use other solvents, for example those mentioned above.

The novel s-triazines of the formula I, in which X represents the azido group, can also be obtained by reacting the chlorotriazine of the formula Ia first with hydrazine to give the 2-hydrazino-4,6-diamino-s-triazine and then reacting this latter further with nitrous acid or an alkali metal nitrite.

The production of the triazine compounds of the formula I is described in more detail in the following Examples. The parts are by weight. Following on the Examples is a list of compounds prepared in analogous manner.

EXAMPLE 1

2-Chloro-4-isopropylamino-6-(1',1'-dichlorocyclopropyl-2'-methylamino)-s-triazine (a) A suspension of 369 g of cyanuric chloride in 1000 ml of ethyl acetate is cooled to $-15°$ C. With good stirring, 124 g of isopropylamine are first added dropwise at $-20°$ C. to $-10°$ C. in the course of 2½ hours, followed by 267 g of a 30% aqueous solution of sodium hydroxide in the course of one hour. The reaction mixture is stirred for a further 1½ hours at the same temperature, then the organic phase is separated, washed with two 100 ml portions of water and dried over sodium sulphate. The solvent is evaporated, to yield an oil from which the 2,4-dichloro-6-isopropylamino-s-triazine precipitates in crystalline form after stirring with petroleum ether at low temperature. Melting point: 46°–47° C.

(b) With efficient stirring, 28 g of 1,1-dichloro-2-aminomethylcyclopropane are first added dropwise at 20°–25° C. to a solution of 38.6 g of 2,4-dichloro-6-isopropylamino-s-triazine in 150 ml of ethyl acetate, followed by the dropwise addition of 26.6 g of an aqueous solution of sodium hydroxide. The reaction mixture is subsequently stirred for 15 to 20 hours at room temperature. The ethyl acetate phase is separated, washed with two 25 ml portions of water and dried over sodium sulphate. The solvent is evaporated, to yield the 2-chloro-4-isopropylamino-6-(1′,1′-dichlorocyclopropyl-2′-methylamino)-s-triazine as a crystalline residue. Melting point: 121°–123° C. (recrystallisation from isopropylether). (Compound 1).

(c) The 1,1-dichloro-2-amino-methyl-cyclopropane used as intermediate was prepared as follows:

223 g of 1,1-dichloro-2-chloromethylcyclopropane and 140 ml of water are charged into an autoclave and 95 g of ammonia gas are introduced under pressure. The reaction mixture is then heated and kept for 20 hours at 90°–100° C. After cooling, the amine phase is separated, dried over sodium hydroxide and then distilled in vacuo over a Vigreux column. The 1,1-dichloro-2-aminomethyl-cyclopropane boils at 60°–62° C./16 torr. $n_D^{20}$: 1.4898.

EXAMPLE 2

2-Methylamino-4-isopropylamino-6-(1′,1′-dichlorocyclopropyl-2′-methylamino-s-triazine 18 g of 2-chloro-4-isopropylamino-6-(1′,1′-dichlorocyclopropyl-2′-methylamino)-s-triazine (see Example 1) are dissolved in 150 ml of acetone and to this solution is added a solution of 3.5 g of trimethylamine in 15 ml of water. Then 3 g of methylmercaptan are introduced at 20°–25° C. and the reaction mixture is stirred for 15 to 20 hours. The solution is then concentrated and the residue is taken up in 150 ml of ethyl acetate, and this solution is washed with two 15 ml portions of water, dried over magnesium sulphate and concentrated. The residual oil is dissolved warm in a small amount of isopropyl ether, whereupon the 2-methylthio-4-isopropylamino-6-(1′,1′-dichlorocyclopropyl-2′-methylamino)-s-triazine crystallises on cooling. Melting point: 76°–78° C. (Compound 2).

EXAMPLE 3

2-Azido-4-isopropylamino-6-(1′,1′-dichlorocyclopropyl-2′-methylamino)-s-triazine A solution of 4.1 g of sodium azide in 50 ml of water is added dropwise at 20°–25° C. to a mixture of 18 g of 2-chloro-4-isopropylamino-6-(1′,1′-dichlorocyclopropyl-2′-methylamino)-s-triazine, 150 ml of acetone, 3.5 g of trimethylamine and 15 ml of water. The reaction mixture is stirred for 15 to 20 hours, then 150 ml of water are added and the precipitated 2-azido-4-isopropylamino-6-(1′,1′-dichlorocyclopropyl-2′-methylamino)-s-triazine is collected by filtration. Melting point: 108°–110° C. (Compound 3).

EXAMPLE 4

2-Methoxy-4-isopropylamino-6-)1′,1′-dichlorocyclopropyl-2′-methylamino-s-triazine 18 g of 2-chloro-4-isopropylamino-6-(1′,1′-dichlorocyclopropyl-2′-methylamino)-s-triazine (see Example 1) are added in portions to a solution of 1.4 g of sodium in 120 ml of methanol at 20°–25° C. About 5 drops of a 40% aqueous solution of trimethylamine are added and the reaction mixture is stirred initially at room temperature and then for 6 hours at about 40° C. Salt which has formed is removed cold by filtration and the methanol is evaporated. After addition of isopropyl ether to the residue, 2-methoxy-4-isopropylamino-6-(1′,1′-dichlorocyclopropyl-2′-methylamino)-s-triazine crystallises. Melting point: 96°–98° C. (Compound 4).

EXAMPLE 5

2-Chloro-4-cyclopropylamino-6-(1′,1′-dichloro-2′-methylcyclopropyl-2′-methylamino)-s-triazine 82 g of 2,4-dichloro-6-cyclopropylamino-s-triazine (prepared analogously to Example 1a), melting point: 107°–108° C.) and 83.8 g of 1,1-dichloro-2-methyl-2-aminomethyl-cyclopropane hydrochloride are suspended in 700 ml of ethyl acetate and 224 g of a 15% aqueous sodium hydroxide solution are added dropwise at 20°–26° C. to the suspension. The reaction mixture is subsequently stirred for 15–20 hours at room temperature and the resulting 2-chloro-4-cyclopropylamino-6-(1′,1′-dichloro-2′-methylcyclopropyl-2′-methylamino)-s-triazine is then collected by filtration. Concentration of the ethyl acetate phase yields further product. Melting point: 170°–171° C. (recrystallisation from ethyl acetate). Compound 29).

EXAMPLE 6

2-Chloro-4,6-bis(1′,1′-dichlorocyclopropyl-2′-methylamino)-s-triazine

A solution of 14 g of 1,1-dichloro-2-methylaminocyclopropane in 25 ml of ethyl acetate and then 13.3 g of a 30% aqueous sodium hydroxide solution are added dropwise at 5° to 15° C. in succession to 9.2 g of cyanuric chloride in 100 ml of ethyl acetate. The reaction mixture is stirred overnight at room temperature and the precipitated 2-chloro-4,6-bis(1′,1′-dichlorocyclopropyl-2′-methylamino)-s-triazine is then collected by filtration. Melting point: 223°–224° (recrystallisation from ethyl acetate). (Compound 17).

EXAMPLE 7

2-Chloro-4-isopropylamino-6-(1′,1′-dichloro-2′-methylcyclopropyl-2′-methylamino)-s-triazine (a) A suspension of 55.3 g of cyanuric chloride in 600 ml of ethyl acetate is treated dropwise at −15° to 10° first with 46.2 g of 1,1-dichloro-2-methyl-2-aminomethylcyclopropane and then with 40 g of a 30% aqueous solution of sodium hydroxide. The mixture is then stirred for 1½ hours at −15° to −5° C., the temperature is raised to 20° C. and, at 20°–26° C., 17.7 g of isopropylamine and then 40 g of a 30% aqueous sodium hydroxide solution are added dropwise and the reaction mixture is stirred overnight at room temperature. After addition of 150 ml of water to the reaction mixture, the organic phase is separated, washed with 150 ml of water and dried over magnesium sulphate. After evaporation of the solvent, the oily residue is dissolved in hot isopropyl ether. The 2-chloro-4-isopropylamino-6-(1',1'-dichloro-2'-methylcyclopropyl-2'-methylamino)-s-triazine crystallises on cooling. Melting point: 116°–118° C. (Compound 21).

(b) The 1,1-dichloro-2-methyl-2-aminomethyl-cyclopropane used as intermediate was prepared as follows:

469 g of 1,1-dichloro-2-methyl-2-chloromethylcyclopropane, 270 ml of water and 138 g of ammonia gas are reacted in an autoclave as described in Example (1c), worked up and distilled. For purification, the fraction boiling at 54°–58° C./13 torr is taken up in ether. By introducing hydrogen chloride gas, the amine is precipitated in the form of the hydrochloride (m.p. 250° C., with decomposition). For reaction with chlorotriazines, the hydrochloride can be used direct or converted into the free amine by treatment with sodium hydroxide solution. Boiling point of the pure 1,1-dichloro-2-methyl-2-aminomethylcyclopropane: 59° C./12 torr; $n_D^{20}$: 1.4897.

(c) The intermediate, 2,4-dichloro-6-(1',1'-dichloro-2'-methylcyclopropyl-2-methylamino)-s-triazine, was also obtained as follows:

13.8 g of cyanuric chloride in 150 ml of ethyl acetate are reacted with 11.8 g of 1,1-dichloro-2-methyl-2-aminomethylcyclopropane and 10 g of 30% aqueous sodium hydroxide solution in the manner described in Example (1a). After working up and recrystallisation as described, the product has a melting point of 113°–115° C.

EXAMPLE 8

2-Chloro-4-isopropylamino-6-(1',1'-dichlorocyclopropyl-2'-methylamino)-s-triazine (a) A suspension of 9.2 g of cyanuric chloride in 100 ml of ethyl acetate is cooled to −15° C. With efficient stirring, firstly 7 g of 1,1-dichloro-2-aminomethylcyclopropane, then 6.6 g of a 30% aqueous sodium hydroxide solution, are added dropwise at −15° to −10° C. Stirring is then continued for about 1½ hours at −10° to 0° C. Then 20 ml of water are added and the phases are separated. The organic phase is washed with 20 ml of water and dried over magnesium sulphate. The solvent is distilled off, leaving an oily residue which crystallises after warming with isopropyl ether. The resulting 2,4-dichloro-6-(1',1'-dichlorocyclopropyl-2'-methylamino)-s-triazine melts at 110°–111° C.

(b) Reaction of the above product in ethyl acetate with the equimolar amount of isopropylamine and 30% aqueous sodium hydroxide solution at 20°–25° C. in a manner analogous to that described in Example (1b) yields 2-chloro-4-isopropylamino-6-(1',1'-dichlorocyclopropylamino)-s-triazine with a melting point of 121°–123° C. (Compound 1).

EXAMPLE 9

2-Cyano-4-isopropylamino-6-(1',1'-dichloro-2'-methylcyclopropyl-2'-methylamino)-s-triazine With stirring, 11.8 g of a 40% aqueous trimethylamine solution are added to a solution of 24.6 g of 2-chloro-4-isopropylamino-6-(1',1'-dichloro-2'-methylcyclopropyl-2'-methylamino)-s-triazine (see Example 7) in 100 ml of acetone. A solution of 5.2 g of potassium cyanide in 15 ml of water is added dropwise at 15°–20° C. in the course of 10 minutes and the reaction mixture is subsequently stirred for 15 to 20 hours. The precipitated reaction product is then collected by filtration and washed with water. The cyano-triazine, which is recrystallised from ethyl acetate/isopropyl ether, has a melting point of 137°–139° C.

| No. | R | $R_1$ | X | Physical constant in °C. |
|---|---|---|---|---|
| 1 | iso $C_3H_7$ | H | Cl | m.p. 121°–123° |
| 2 | iso $C_3H_7$ | H | $SCH_3$ | m.p. 76°–78° |
| 3 | iso $C_3H_7$ | H | $N_3$ | m.p. 108°–110° |
| 4 | iso $C_3H_7$ | H | $OCH_3$ | m.p. 96°–98° |
| 5 | $C_2H_5$ | H | Cl | m.p. 200°–201° |
| 6 | $C_2H_5$ | H | $N_3$ | m.p. 86°–88° |
| 7 | $C_2H_5$ | H | $OCH_3$ | m.p. 115°–117° |
| 8 | $C_2H_5$ | H | $SCH_3$ | m.p. 40°–42° |
| 9 | $-\underset{\underset{CH_3}{\mid}}{\overset{CH_3}{\mid}}{C}-CN$ | H | Cl | m.p. 169°–170° |
| 10 | $-\underset{\underset{CH_3}{\mid}}{\overset{CH_3}{\mid}}{C}-CN$ | H | $OCH_3$ | m.p. 146°–148° |
| 11 | $-\underset{\underset{CH_3}{\mid}}{\overset{CH_3}{\mid}}{C}-CN$ | H | $N_3$ | m.p. 183°–185° |
| 12 | $-\underset{\underset{CH_3}{\mid}}{\overset{CH_3}{\mid}}{C}-CN$ | H | $SCH_3$ | m.p. 142°–143° |
| 13 | tert $C_4H_9$ | H | Cl | m.p. 151°–153° |
| 14 | tert $C_4H_9$ | H | $N_3$ | m.p. 106°–108° |
| 15 | tert $C_4H_9$ | H | $OCH_3$ | m.p. 102°–103° |
| 16 | tert $C_4H_9$ | H | $SCH_3$ | m.p. 47°–29° |
| 17 | $-CH_2-$(Cl,Cl-cyclopropyl) | H | Cl | m.p. 223°–224° |
| 18 | $-CH_2-$(Cl,Cl-cyclopropyl) | H | $N_3$ | |
| 19 | $-CH_2-$(Cl,Cl-cyclopropyl) | H | $OCH_3$ | |
| 20 | $-CH_2-$(Cl,Cl-cyclopropyl) | H | SCH | |
| 21 | iso $C_3H_7$ | $CH_3$ | Cl | m.p. 116°–118° |
| 22 | iso $C_3H_7$ | $CH_3$ | $OCH_3$ | m.p. 98°–100° |
| 23 | iso $C_3H_7$ | $CH_3$ | $N_3$ | m.p. 90°–92° |
| 24 | iso $C_3H_7$ | $CH_3$ | $SCH_3$ | m.p. 125°–127° |
| 25 | $-CH_2-$(Cl,Cl,CH_3-cyclopropyl) | $CH_3$ | Cl | m.p. 159°–160° |
| 26 | $-CH_2-$(Cl,Cl,CH_3-cyclopropyl) | $CH_3$ | $OCH_3$ | m.p. 136°–138° |
| 27 | $-CH_2-$(Cl,Cl,CH_3-cyclopropyl) | $CH_3$ | $N_3$ | |
| 28 | $-CH_2-$($CH_3,CH_3,CH_3$-cyclopropyl) | | $SCH_3$ | m.p. 92°–94° |
| 29 | (cyclopropyl) | $CH_3$ | Cl | m.p. 170°–171° |

-continued

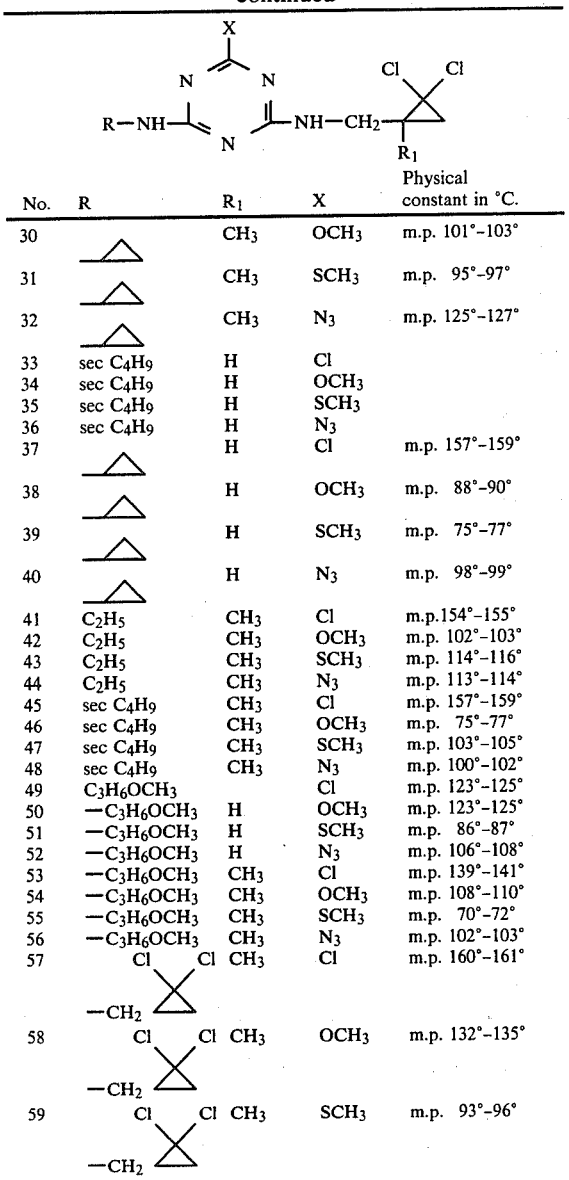

| No. | R | R₁ | X | Physical constant in °C. |
|---|---|---|---|---|
| 30 | △ | CH₃ | OCH₃ | m.p. 101°–103° |
| 31 | △ | CH₃ | SCH₃ | m.p. 95°–97° |
| 32 | △ | CH₃ | N₃ | m.p. 125°–127° |
| 33 | sec C₄H₉ | H | Cl | |
| 34 | sec C₄H₉ | H | OCH₃ | |
| 35 | sec C₄H₉ | H | SCH₃ | |
| 36 | sec C₄H₉ | H | N₃ | |
| 37 | △ | H | Cl | m.p. 157°–159° |
| 38 | △ | H | OCH₃ | m.p. 88°–90° |
| 39 | △ | H | SCH₃ | m.p. 75°–77° |
| 40 | △ | H | N₃ | m.p. 98°–99° |
| 41 | C₂H₅ | CH₃ | Cl | m.p. 154°–155° |
| 42 | C₂H₅ | CH₃ | OCH₃ | m.p. 102°–103° |
| 43 | C₂H₅ | CH₃ | SCH₃ | m.p. 114°–116° |
| 44 | C₂H₅ | CH₃ | N₃ | m.p. 113°–114° |
| 45 | sec C₄H₉ | CH₃ | Cl | m.p. 157°–159° |
| 46 | sec C₄H₉ | CH₃ | OCH₃ | m.p. 75°–77° |
| 47 | sec C₄H₉ | CH₃ | SCH₃ | m.p. 103°–105° |
| 48 | sec C₄H₉ | CH₃ | N₃ | m.p. 100°–102° |
| 49 | C₃H₆OCH₃ | | Cl | m.p. 123°–125° |
| 50 | —C₃H₆OCH₃ | H | OCH₃ | m.p. 123°–125° |
| 51 | —C₃H₆OCH₃ | H | SCH₃ | m.p. 86°–87° |
| 52 | —C₃H₆OCH₃ | H | N₃ | m.p. 106°–108° |
| 53 | —C₃H₆OCH₃ | CH₃ | Cl | m.p. 139°–141° |
| 54 | —C₃H₆OCH₃ | CH₃ | OCH₃ | m.p. 108°–110° |
| 55 | —C₃H₆OCH₃ | CH₃ | SCH₃ | m.p. 70°–72° |
| 56 | —C₃H₆OCH₃ | CH₃ | N₃ | m.p. 102°–103° |
| 57 | —CH₂—CCl₂△ | CH₃ | Cl | m.p. 160°–161° |
| 58 | —CH₂—CCl₂△ | CH₃ | OCH₃ | m.p. 132°–135° |
| 59 | —CH₂—CCl₂△ | CH₃ | SCH₃ | m.p. 93°–96° |

-continued

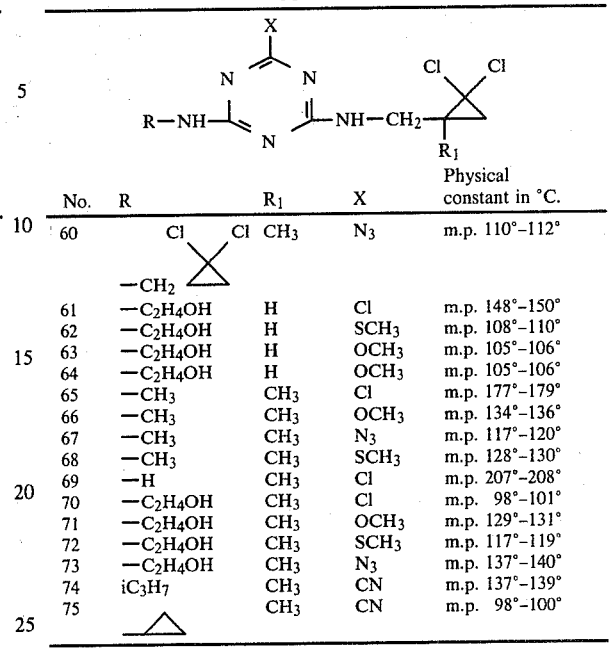

| No. | R | R₁ | X | Physical constant in °C. |
|---|---|---|---|---|
| 60 | —CH₂—CCl₂△ | CH₃ | N₃ | m.p. 110°–112° |
| 61 | —C₂H₄OH | H | Cl | m.p. 148°–150° |
| 62 | —C₂H₄OH | H | SCH₃ | m.p. 108°–110° |
| 63 | —C₂H₄OH | H | OCH₃ | m.p. 105°–106° |
| 64 | —C₂H₄OH | H | OCH₃ | m.p. 105°–106° |
| 65 | —CH₃ | CH₃ | Cl | m.p. 177°–179° |
| 66 | —CH₃ | CH₃ | OCH₃ | m.p. 134°–136° |
| 67 | —CH₃ | CH₃ | N₃ | m.p. 117°–120° |
| 68 | —CH₃ | CH₃ | SCH₃ | m.p. 128°–130° |
| 69 | —H | CH₃ | Cl | m.p. 207°–208° |
| 70 | —C₂H₄OH | CH₃ | Cl | m.p. 98°–101° |
| 71 | —C₂H₄OH | CH₃ | OCH₃ | m.p. 129°–131° |
| 72 | —C₂H₄OH | CH₃ | SCH₃ | m.p. 117°–119° |
| 73 | —C₂H₄OH | CH₃ | N₃ | m.p. 137°–140° |
| 74 | iC₃H₇ | CH₃ | CN | m.p. 137°–139° |
| 75 | △ | CH₃ | CN | m.p. 98°–100° |

To determine the herbicidal action, the following tests were carried out:

Post-emergence application

In a greenhouse, plant seeds were sown in pots having a diamater of 12–15 cm, so that about 8 to 20 plants were able to develop in each pot. The pots were then left to stand for about 2 weeks until the plants had emerged and reached the two- to three-leaf stage. The pots were then sprayed with a spray mixture of the substance to be tested in a concentration corresponding to a rate of application of 4, 2, 1 and 0.5 kg/hectare respectively. The pots were then further reared in the greenhouse under optimum conditions, i.e. at 50–70% relative humidity and at a temperature of 20°–23° C. and with regular watering. The test was evaluated after 20 days and the state of the plants was assessed in accordance with the following rating:

9 = plant flourishes normally as untreated control
2–8 = intermediate stages of damage to the plant
1 = plant withered The results are reported in the following table:

| | Compound | | | | | | | | | | | | | | | |
|---|---|---|---|---|---|---|---|---|---|---|---|---|---|---|---|---|
| | 1 | | | | 2 | | | | ATRAZIN® | | | | IGRAN® | | | |
| | rate of application in kg/ha | | | | | | | | | | | | | | | |
| | 4 | 2 | 1 | ½ | 4 | 2 | 1 | ½ | 4 | 2 | 1 | ½ | 4 | 2 | 1 | ½ |
| Plants | | | | | | | | | | | | | | | | |
| barley | 4 | 7 | 9 | 9 | 6 | 6 | 7 | 8 | 1 | 1 | 3 | 6 | 1 | 1 | 4 | 8 |
| wheat | 8 | 9 | 9 | 9 | 7 | 8 | 9 | 9 | 1 | 1 | 3 | 4 | 3 | 4 | 6 | 9 |
| maize | 8 | 8 | 9 | 9 | 7 | 8 | 9 | 9 | 8 | 9 | 9 | 9 | 6 | 6 | 6 | 6 |
| millet | 9 | 9 | 9 | 9 | 7 | 7 | 8 | 9 | 8 | 9 | 9 | 9 | 6 | 7 | 8 | 7 |
| rice | 8 | 9 | 9 | 9 | 9 | 9 | 9 | 9 | 1 | 1 | 1 | 1 | 2 | 2 | 2 | 7 |
| soya | 3 | 6 | 7 | 8 | 4 | 5 | 6 | 7 | 1 | 1 | 1 | 2 | 2 | 2 | 2 | 2 |
| cotton | 7 | 8 | 9 | 9 | 3 | 3 | 4 | 5 | 1 | 1 | 1 | 2 | 1 | 1 | 1 | 2 |
| avena fatua | 7 | 8 | 9 | 9 | 8 | 9 | 9 | 9 | 1 | 1 | 1 | 1 | 2 | 2 | 2 | 4 |
| lolium perenne | 7 | 9 | 9 | 9 | 6 | 7 | 8 | 8 | 2 | 2 | 2 | 2 | 1 | 1 | 2 | 4 |
| alopecurus myosuroides | 2 | 2 | 7 | 9 | 2 | 4 | 7 | 9 | 1 | 1 | 2 | 2 | 1 | 2 | 2 | 4 |
| cyperus escultentus | 9 | 9 | 9 | 9 | 9 | 9 | 9 | 9 | 7 | 8 | 9 | 9 | 5 | 6 | 8 | 9 |
| rottboellia exaltata | 9 | 9 | 9 | 9 | 9 | 9 | 9 | 9 | 9 | 9 | 9 | 9 | 2 | 3 | 5 | 7 |
| digitaria sangui- | | | | | | | | | | | | | | | | |

-continued

|  | Compound | | | | | | | | | | | | | | | |
|---|---|---|---|---|---|---|---|---|---|---|---|---|---|---|---|---|
|  | 1 | | | | 2 | | | | ATRAZIN® | | | | IGRAN® | | | |
|  | rate of application in kg/ha | | | | | | | | | | | | | | | |
|  | 4 | 2 | 1 | ½ | 4 | 2 | 1 | ½ | 4 | 2 | 1 | ½ | 4 | 2 | 1 | ½ |
| nalis | 7 | 9 | 9 | 9 | 2 | 2 | 7 | 7 | 1 | 4 | 4 | 4 | 1 | 1 | 1 | 1 |
| setaria italica | 7 | 8 | 8 | 9 | 1 | 1 | 7 | 7 | 1 | 3 | 7 | 7 | 1 | 1 | 1 | 1 |
| echinochloa crus galli | 4 | 4 | 5 | 8 | 2 | 2 | 8 | 9 | 1 | 1 | 1 | 2 | 1 | 1 | 1 | 1 |
| beta vulgaris | 2 | 3 | 4 | 7 | 1 | 1 | 1 | 1 | 1 | 1 | 1 | 1 | 1 | 1 | 1 | 1 |
| sesbania exaltata | 1 | 1 | 1 | 9 | 2 | 3 | 3 | 9 | 1 | 1 | 1 | 1 | 1 | 1 | 1 | 1 |
| amaranthus retroflexus | 6 | 7 | 7 | 8 | 1 | 2 | 2 | 3 | 1 | 2 | 2 | 2 | 1 | 1 | 1 | 2 |
| sinapis alba | 1 | 1 | 1 | 6 | 1 | 1 | 1 | 1 | 1 | 1 | 1 | 1 | 1 | 1 | 1 | 1 |
| ipomoea purpurea | 2 | 7 | 8 | 9 | 3 | 4 | 6 | 7 | 1 | 1 | 1 | 1 | 1 | 1 | 1 | 1 |
| galium aparine | 4 | 7 | 8 | 9 | 7 | 8 | 8 | 9 | 1 | 2 | 2 | 2 | 1 | 2 | 5 | 9 |
| pastinaca sativa | 9 | 9 | 9 | 9 | 3 | 3 | 4 | 9 | 1 | 1 | 1 | 1 | 1 | 3 | 3 | 4 |
| taraxacum officinalis | 7 | 8 | 8 | 8 | 6 | 6 | 6 | 7 | 1 | 1 | 1 | 1 | 2 | 2 | 3 | 3 |
| matricaria chamomille | 9 | 9 | 9 | 9 | 2 | 4 | 7 | 8 | 1 | 1 | 1 | 1 | 1 | 1 | 1 | 1 |
| sida spinosa | 9 | 9 | 9 | 9 | 7 | 7 | 8 | 8 | 1 | 1 | 4 | 4 | 2 | 2 | 2 | 4 |

ATRAZIN® is 2-chloro-4-ethylamino-6-isopropylamino-s-triazine known from Swiss patent 329,277
IGRAN® is 2-methylthio-4-ethylamino-6-tert-butylamino-s-triazine, known from Swiss patent 470,136.

In contrast to the known compounds, the compounds of the present invention do not damage rice in the post-emergence application.

Herbicidal tests with rice

In a greenhouse, plastic tubs measuring 30×50 cm and 25 cm deep are filled with soil to a height of about 7 cm. Then rice and weeds are sown in rows. The soil is kept very moist. When the plants have germinated, water is added until it stands above the soil. The water level is adjusted in accordance with the height of the plants and reaches a maximum level of 5 cm before the conclusion of the test.

In some tests the rice is reared in separate plastic tubs and after 3 weeks, when the plants have 2 1/2–4 leaves, is transplanted into the tubs with the weeds at a water level of 2 1/2–3 cm. The application is made about 2 weeks after the plants have been sown, when these—depending on the species—have developed 2 to 8 leaves. Two application methods are used.

Spraying

The rice and weeds, the tips of which project above the level of the water, are sprayed from fine jets with a concentrated active substance solution or emulsion in amounts corresponding to the indicated concentration per unit of area.

Instilling or granulate method

The active substance is processed to granulate form and the granules are then spread between the rows of plants in the calculated concentrations per unit of area.

If the active substance is not formulated as granulate, then a concentrated solution or emulsion is used, which is instilled between the rows of plants in the calculated rates of application using pipettes. The test is evaluated 3 weeks after the application of the active substance, the state of the plants being assessed in accordance with the above rating. The results are reported in the following table:

Post-emergence application, sprayed:

|  | Compound | | | | | | | | | | | |
|---|---|---|---|---|---|---|---|---|---|---|---|---|
|  | 1 | | | | 2 | | | | Igran® | | | |
|  | rate of application in kg/ha | | | | | | | | | | | |
|  | 4 | 2 | 1 | ½ | 4 | 2 | 1 | ½ | 4 | 2 | 1 | ½ |
| Plants | | | | | | | | | | | | |
| rice "Caloro" (sown) | 4 | 5 | 7 | 9 | 4 | 4 | 8 | 9 | 1 | 2 | 2 | 4 |
| rice "IR 8" (transplanted) | 8 | 9 | 9 | 9 | 7 | 7 | 9 | 9 | 2 | 3 | 3 | 7 |
| echinochloa crus galli | 3 | 3 | 3 | 7 | 1 | 2 | 4 | 8 | 1 | 1 | 1 | 1 |
| cyperus difformis | 2 | 2 | 2 | 2 | 1 | 1 | 1 | 2 | 1 | 1 | 1 | 2 |
| rotala indica | 1 | 1 | 1 | 1 | 1 | 1 | 1 | 1 | 1 | 1 | 1 | 1 |
| ammannia sp. | 1 | 1 | 1 | 1 | 1 | 1 | 1 | 1 | 1 | 1 | 1 | 1 |
| alisma sp. | 1 | 1 | 1 | 2 | 1 | 1 | 1 | 1 | 1 | 1 | 1 | 2 |
| vandellia sp. | 1 | 2 | 2 | 4 | 1 | 1 | 2 | 4 | 1 | 1 | 2 | 2 |

Post-emergence application, instilling method:

|  | Compound | | | | | | | | | | | |
|---|---|---|---|---|---|---|---|---|---|---|---|---|
|  | 1 | | | | 2 | | | | Igran® | | | |
|  | rate of application in kg/ha | | | | | | | | | | | |
|  | 4 | 2 | 1 | ½ | 4 | 2 | 1 | ½ | 4 | 2 | 1 | ½ |
| Plants | | | | | | | | | | | | |
| rice "Caloro" (sown) | 6 | 7 | 8 | 9 | 8 | 9 | 9 | 9 | 1 | 2 | 5 | 6 |
| rice "IR 8" (transplanted) | 8 | 9 | 9 | 9 | 9 | 9 | 9 | 9 | 1 | 1 | 2 | 3 |
| echinochloa crus galli | 7 | 7 | 8 | 9 | 6 | 7 | 8 | 9 | 1 | 1 | 2 | 2 |
| cyperus difformis | 1 | 2 | 3 | 3 | 1 | 2 | 2 | 3 | 1 | 1 | 1 | 2 |
| rotala indica | 1 | 1 | 1 | 2 | 1 | 1 | 1 | 1 | 1 | 1 | 1 | 1 |
| ammannia sp. | 1 | 1 | 1 | 1 | 1 | 1 | 3 | 6 | 1 | 1 | 1 | 1 |
| alisma sp. | 1 | 1 | 1 | 3 | 1 | 1 | 1 | 3 | 1 | 1 | 1 | 1 |
| vandellia sp. | 2 | 3 | 4 | 4 | 1 | 1 | 2 | 3 | 1 | 1 | 1 | 1 |

In contrast to the simultaneously treated weeds, the rice in these tests was not damaged by the compounds of the invention.

Growth inhibition of grass in a field test

The test area is an established area of grass in the open consisting of *Lolium perenne* (20%), *Poa pratensis* (25%), *Festuca rubra* (45%) and *Agrostis tenuis* (10%).

When the grass has reached a height of 9 cm after the first cutting in spring, parcels measuring 3 m² are uniformly sprayed with aqueous preparations of the indicated active substances. The rate of application is 5 kg and 2.5 kg of active substance per hectare. Untreated parcels of the same size as well as strips between the individual parcels are used as controls.

The average growth in height of the top grasses in the treated and untreated parcels is measured 1, 4 and 12 weeks after the application of the active substances.

In this test, the compounds of the invention exhibited a good growth-inhibiting action.

These compounds are advantageously formulated as a herbicidal composition for use in agriculture and applied in rates of application between 0.1 and 10 kg of active substance per hectare, preferably between 0.2 and 4 kg per hectare. The active substances are formulated together with one or more carriers, emulsifiers and other additives. Such "vehicles" can be solid or liquid. Solvents, diluents, dispersants, wetting agents, tackifiers, thickeners or binders can be used.

The compositions according to the invention are obtained in known manner by intimately mixing and/or grinding active substances of the formula I with suitable carriers, with or without the addition of dispersants or solvents which are inert towards the active substances. The active substances may be processed to the following formulations:

Solid formulations:
dusts, tracking powders, granules (coated granules, impregnated granules and homogeneous granules); active substance concentrates which are dispersible in water:
wettable powders, pastes, emulsions; emulsion concentrates.

Liquid formulations:
solutions.

Solid formulations (dusts, tracking powders, granules) are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The granular size of the carriers for dusts is advantageously up to approx. 0.1 mm, for tracking powders approx. 0.075 go 0.2 mm, and for granules 0.2 mm or greater.

The concentrations of active substance in the solid formulations are 0.5 to 80%.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable agglutinants are: olein/- chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents. The concentrations of active substance in these compositions is 5 to 80%.

Wettable powders and pastes are obtained by mixing and grinding the active substances with dispersing agents and pulverulent carriers in suitable devices until homogeneity is attained. Suitable carriers are, for example, those already mentioned for the solid formulations. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalenesulphonic acids with phenol and formaldehyde, as well as alkali metal, ammonium and alkaline earth metal salts of ligninsulphonic acid, in addition, alkylarylsulphonates, alkali metal and alkaline earth metal salts of dibutylnaphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyldilaurylammonium chloride and fatty acid alkali metal and alkaline earth metal salts.

Suitable anti-foam agents are for example silicones.

The active substances are mixed, ground sieved and strained with the above additives such that, in wettable powders, the solid particle size of 0.02 to 0.04 mm and in pastes, of 0.03 mm, is not exceeded. Emulsifiable concentrates and pastes are manufactured by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active substances and may not be readily inflammable.

Furthermore, the compositions of the invention can be applied in the form of solutions. For this purpose the active substances or several active substances of the general formula I are dissolved in suitable organic solvents, mixtures of solvents, or in water. Aliphatic and aromatic hydrocarbons, chlorinated derivatives thereof, alkylnaphthalenes and mineral oils, by themselves or in admixture, can be used as organic solvents. The solutions will contain the active substances in a concentration from 1 to 20%.

The compositions of this invention can be mixed with other biocidally active substances or agents. Thus in order to broaden the activity spectrum, the compositions may contain, for example, insecticides, fungicides, bactericides, fungistats, bacteriostats or nematocides, in addition to the cited compounds of the general formula I. The compositions of the invention may also contain plant fertilisers, trace elements etc.

Formulations of the novel active compounds of the formula I are described hereinafter. The parts denote parts by weight.

Granules

The following substances are used to prepare 5% granules:
5 2-chloro-4-isopropylamino-6-(1',1'-dichlorocyclopropyl-2'-methylamino)-s-triazine,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to prepare (a) a 50%, (b) a 25% and (c) a 10% wettable powder:

(a)

50 parts of 2-methoxy-4-isopropylamino-6-(1',1'-dichlorocyclopropyl-2'-methylamino)-s-triazine,
5 parts of sodium dibutylnaphthalenesulphate,
3 parts of naphthalenesulphonic acid/phenolsulphonic acid/formaldehyde condensate (3:2:1),
20 parts of kaolin,
22 parts of Champagne chalk;

(b) 25 parts of the above active substance,
5 parts of the sodium salt of oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin.

(c)

10 parts of the above active substance,
3 parts of a mixture of the sodium salts of saturated fatty alcohol sulphates,
5 parts of naphthalenesulphonic acid/formaldehyde condensate,
82 parts of kaolin.

The respective active substance is applied to the corresponding carriers (kaolin and chalk) and then these are mixed and ground, to yield wettable powders of excellent wettability and suspension power. By diluting these wettable powders with water it is possible to obtain suspensions of the desired concentration. These suspensions are suitable for controlling weeds and grasslike weeds in crops of cultivated plants.

Paste

The following substances are used to prepare a 45% paste:

45 parts of 2-chloro-4-isopropylamino-6-(1',1'-dichlorocyclopropyl-2'-methylamino)-s-triazine,
5 parts of sodium aluminium silicate,
14 parts of cetyl polyglycol ether with 8 moles of ethylene oxide,
1 part ofoleyl polyglycol ether with 5 moles of ethylene oxide,
2 parts of spindle oil,
10 parts of water.

The active substance is intimately mixed with the additives in appropriate devices and ground. A paste is obtained from which, by dilution with water, it is possible to manufacture suspensions of the desired concentration.

Emulsifiable Concentrate

The following ingredients are mixed to prepare 25% emulsifiable concentrate:
25 parts of 2-chloro-4-isopropylamino-6-(1',1'-dichloro-2'-methylcyclopropyl-2'-methylamino)-s-triazine,
5 parts of a mixture of nonylphenolpolyoxyethylene and calcium dodecylbenzenesulphonate,
35 parts of 3,5,5-trimethyl-2-cyclohexen-1-one,
35 parts of dimethyl formamide.

This concentrate can be diluted with water to give emulsions in suitable concentrations. Such emulsions are suitable for controlling weeds in crops of cultivated plants, for example cotton, maize etc.

I claim:

1. A compound of formula I

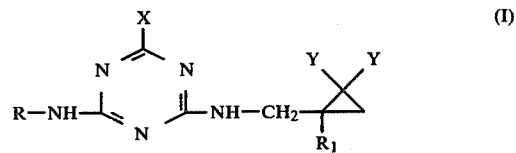

wherein R represents hydrogen, $C_1$–$C_6$ alkyl which is unsubstituted or substituted by cyano, hydroxy, $C_1$–$C_4$ alkoxy, cyclopropyl, methylcyclopropyl or the radical

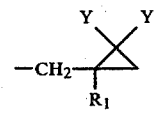

wherein
$R_1$ represents hydrogen or methyl
X represents chlorine, methoxy, methylthio, azido or cyano and
Y represents a halogen atom.

2. 2-Chloro-4-isopropylamino-6-(1',1'-dichlorocyclopropyl-2-methylamino)-s-triazine according to claim 1.

3. 2-Methylthio-4-isopropylamino-6-(1',1'-dichlorocyclopropyl-2-methylamino)-s-triazine according to claim 1.

4. 2-Methoxy-4-ethylamino-6-(1',1-dichloro-2'-methylcyclopropyl-2-methylamino)-s-triazine according to claim 1.

* * * * *